United States Patent
Shen et al.

(10) Patent No.: US 9,492,486 B2
(45) Date of Patent: Nov. 15, 2016

(54) PREPARATION OF BEE VENOM WITH ALLERGENIC COMPONENTS REMOVED

(71) Applicant: CHUNG JIN BIOTECH CO., LTD, Gyeonggi-do (KR)

(72) Inventors: Chang Zhe Shen, Gyeonggi-do (KR); Ha Young Won, Gyeonggi-do (KR); Seung Ju Kim, Gyeonggi-do (KR); Choul Goo Kim, Gyeonggi-do (KR); Ji Yeon Lee, Gyeonggi-do (KR); Yeon Hee Shin, Gyeonggi-do (KR); Seon Young Lee, Gyeonggi-do (KR); Jung Keun Park, Gyeonggi-do (KR); Eui Kyung Kim, Gyeonggi-do (KR)

(73) Assignee: CHUNG JIN BIOTECH CO., LTD, Gyeonggi-do (KR)

(*) Notice: Subject to any disclaimer, the term of this patent is extended or adjusted under 35 U.S.C. 154(b) by 140 days.

(21) Appl. No.: 14/382,016

(22) PCT Filed: Jun. 7, 2013

(86) PCT No.: PCT/KR2013/005016
§ 371 (c)(1),
(2) Date: Aug. 29, 2014

(87) PCT Pub. No.: WO2014/196674
PCT Pub. Date: Dec. 11, 2014

(65) Prior Publication Data
US 2016/0151426 A1    Jun. 2, 2016

(51) Int. Cl.
*A61K 35/64* (2015.01)
*A61K 38/00* (2006.01)
*A61Q 19/02* (2006.01)
*A61Q 19/08* (2006.01)
*A61K 8/98* (2006.01)

(52) U.S. Cl.
CPC ............ *A61K 35/64* (2013.01); *A61K 8/987* (2013.01); *A61Q 19/02* (2013.01); *A61Q 19/08* (2013.01); *A61K 2800/72* (2013.01)

(58) Field of Classification Search
None
See application file for complete search history.

(56) References Cited

FOREIGN PATENT DOCUMENTS

| CN | 102973483 A | * | 3/2013 | ............... A61K 8/65 |
| KR | 10-2012-0003178 | | 1/2012 | |

OTHER PUBLICATIONS

English translation of CN102973483A obtained from Google Patent on Apr. 20, 2016.*
Archives of Biochemistry and Biophysics, vol. 171(2), pp. 661-671(1976).
Biochemical and Biophysical Research Communications, vol. 330, pp. 1048-1054(2005).

* cited by examiner

*Primary Examiner* — Robert T Crow
*Assistant Examiner* — John P Nguyen
(74) *Attorney, Agent, or Firm* — Adam Warwick Bell; Matthew Rupert Kaser (57) ABSTRACT

Disclosed is a method for manufacturing a separated and purified bee venom (separated PBV) not possessing allergy-triggering effects by reducing or eliminating allergy-inducing components contained in a bee venom via ultrafiltration, thereby producing a PVB with desirable pharmacological effects while fundamentally blocking allergies that may be induced by the same.

2 Claims, 6 Drawing Sheets

PREPARATION OF BEE VENOM WITH ALLERGENIC COMPONENTS REMOVED

TECHNICAL FIELD

The present invention relates, in general, to a method for manufacturing a separated and purified bee venom (separated PBV) containing no allergenic components and, more particularly, to a method for manufacturing a separated PBV without allergenic components by reducing or eliminating allergy-inducing components contained in the bee venom via ultrafiltration, thereby providing a PBV capable of providing pharmacological effects while fundamentally blocking allergic reactions induced by the same.

BACKGROUND ART

Generally, bee venom refers to a toxin possessed by bees, which is known to aid in the alleviation of arthritis, arteriosclerosis, and lower back pains; and is also effectively used in the treatment of skin wounds, improvement of the immune system via antibacterial and anti-inflammatory responses, cosmetic treatments such as skin whitening and wrinkle improvement, etc.

Purified bee venom (PBV) is a product obtained from bee venom collected from bees using a bee venom collector after the bee venom goes through a series of processes including natural drying, purification, sterilization and lyophilization, etc. The PBV and raw bee venom are known to have similar physiological activities.

The constitutional components of a PBV with physiological activities are shown in Table 1 below.

TABLE 1

| | Components | Pharmacological Actions |
|---|---|---|
| Peptides | melittin | cell lysis, anti-inflammation, immune response |
| | apamin | Neuralgia relief, pain relief, anti-inflammation, immune response |
| | MCD-peptide 401 | anti-inflammation |
| | adolapin | anti-inflammation, pain relief, antipyretic action |
| | protease inhibitor | inhibition of lysis of proteins and esters, anti-inflammation |
| | secapin | sedating hypothermia |
| | tertiapin | degranulation of mast cells |
| | procamine A, B | radiation protection-related action |
| Proteins (Enzyme) | hyaluronidase | histologic reaction, antigenic component |
| | phospholipase A2 | destruction of cell structure, hemolysis, catalytic action |
| | α-glucosidase | promotion of antibody function |
| | phosphotase | promotion of antibody function |
| | lysophospholipase | inhibition of phospholipase A2 activity |
| Amines | histamine | hypotensive action, intestinal contraction, promotion of gastric acid release |
| | dopamine | neurotransmitter |

The PBV consists of more than 40 different kinds of components including peptides, proteins (e.g., enzymes), low molecular active amines, etc. As shown in Table 1, the active ingredients of the PBV are peptides (apamin, melittin, and MCD), active amines (histamine and dopamin), amino acids, etc., all having a molecular weight of 11 kDa (kilodalton) or less.

Among the various bee venom components, a protein component includes phospholipase A2 with a molecular weight of 13 kDa or higher, hyaluronidase, phosphatase, α-glucosidase, etc., which are mainly involved in physiological activities such as destruction of blood cell membranes, blood coagulation, vasodilation and vasopermeability, promotion of blood circulation and protein hydrolysis.

In particular, phospholipase A2 and hyaluronidase are bee venom components that can induce strong allergic reactions which may cause serious safety issues in some people having hypersensitivity thereto (Stefan Bogdanov; Bee Venom: composition, Health, Medicine: A Review, *Bee Product Science* (2011)).

Due to the adverse effects of the bee venom as described above, its efficient dose is limited, which again limits its physiological effects, thus preventing its intrinsic effects from being exhibited.

Korean Patent Application Publication No. 10-2012-0003178 relates to a composition with skin lightening and moisturizing effects containing bee venom extracts as active ingredients, and describes a composition or a cosmetic composition with skin lightening and moisturizing effects containing pretreated bee venom or bee venom extracts.

However, the related arts as in the above method fail to include a step to remove phospholipase A2 and hyaluronidase, which are strong inducers of allergic reactions. Accordingly, the use of the composition or cosmetic composition containing the bee venom extracts, manufactured according to the conventional method, as active ingredients by a person hypersensitive to bee venom may cause very serious safety issues.

Additionally, a method to add an inhibitor to prevent allergic reactions has been suggested but it was proven not advantageous because it could not completely solve the allergy issue and adverse reactions may occur due to the allergic reaction inhibitor.

Additionally, a method to remove phospholipase A2 and hyaluronidase via high performance liquid chromatography (HPLC) or gel filtration has also been suggested but they too were not advantageous because of the drastic decrease in yield during the isolation or purification process and difficulty in the large-scale production of the same.

DISCLOSURE

Technical Problem

Accordingly, the present invention has been made keeping in mind the above problems occurring in the prior art, and an object of the present invention is to provide a method for manufacturing a separated PBV, fundamentally safe from triggering allergic reactions, by eliminating phospholipase A2 and hyaluronidase, strong inducers of allergic reactions, from the PBV via ultrafiltration.

Another object of the present invention is to provide a method for manufacturing a separated PBV, fundamentally safe from triggering allergic reactions, by eliminating hyaluronidase while reducing phospholipase A2, which are both strong inducers of allergic reactions, from the PBV via ultrafiltration.

A further object of the present invention is to provide a method for a large-scale production of a separated PBV with an improved yield by eliminating allergenic components contained in the PBV via ultrafiltration.

Yet another object of the present invention is to provide a cosmetic containing a separated PBV which includes the separated PBV of the present invention.

However, the objects of the present invention are not limited thereto and other objects not described above may be clearly understood by the people in the related art based on the description given herein below.

Technical Solution

In order to accomplish the above objects, the present invention provides a method for manufacturing a separated PBV, including: a first step of preparing a PBV powder; a second step of preparing a bee venom liquid by mixing the PBV powder with distilled water; a third step of removing allergenic components contained in the bee venom liquid via ultrafiltration through a membrane having a cut-off size of 10 kDa; and a fourth step of obtaining a separated PBV with the allergenic components removed; wherein the distilled water to be mixed with the PBV powder in the second step is used in the range of from 1000 mL to 1500 mL per 1 g of the purified bee venom powder, the allergenic components removed through the ultrafiltration membrane in the third step are phospholipase A2 and hyaluronidase, and the separated PBV obtained in the fourth step contains 4 wt % or higher of apamin, and 50 wt % or higher of melittin.

Additionally, the method for manufacturing a separated PBV of the present invention includes a first step of preparing a PBV powder; a second step of preparing a bee venom liquid by mixing the PBV powder with distilled water; a third step of removing allergenic components contained in the bee venom liquid via ultrafiltration through a membrane having a cut-off size of 30 kDa; and a fourth step of obtaining a separated PBV removed of the allergenic components; wherein the distilled water to be mixed with the PBV powder in the second step is used in the range of from 100 mL to 200 mL per 1 g of the PBV powder; the allergenic components removed through the ultrafiltration membrane in the third step are hyaluronidase; and the separated PBV obtained in the fourth step contains 2.5 wt % or higher of apamin, 45 wt % or higher of melittin, and 1 wt % or less of phospholipase A2.

Additionally, the present invention provides a cosmetic containing a separated PBV which includes the separated PBV of the present invention as an active ingredient.

Advantageous Effects

The method of manufacturing a separated PBV of the present invention has the advantage that it can provide a separated PBV fundamentally safe from triggering allergic reactions by eliminating phospholipase A2 and hyaluronidase, which are strong inducers of allergic reactions, from the separated PBV.

Additionally, the method of manufacturing a separated PBV of the present invention has the advantage that it can provide a separated PBV fundamentally safe from triggering allergic reactions by eliminating hyaluronidase while maximally reducing phospholipase A2 (both are strong inducers of allergic reactions) via ultrafiltration.

Additionally, the method of manufacturing a separated PBV of the present invention has the advantage that it can improve the yield of the separated PBV while enabling its large-scale production by eliminating the allergenic components contained in the PBV via ultrafiltration.

Additionally, the cosmetic of the present invention, which contains the separated PBV manufactured according to a method of the present invention as an active ingredient, has the advantage that it has an anti-wrinkle effect and a whitening effect due to the bee venom contained therein while being fundamentally safe from triggering allergic reactions.

BEST MODE

With reference to the accompanying drawings, the present invention will be described in detail herein below. However, in the following description of the invention, if the related known functions or specific instructions on configuring the gist of the present invention unnecessarily obscure the gist of the invention, the detailed description thereof will be omitted.

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

It will be understood that when an element is referred to as being "coupled" or "connected" to another element, it may be directly coupled or connected to the other element or an intervening element(s) may be present therebetween. In contrast, it should be understood that when an element is referred to as being "directly coupled" or "directly connected" to another element, there are no intervening element(s) present. Other expressions that explain the relationship between elements, such as "between," "directly between," "adjacent to," or "directly adjacent to," should be construed in the same way.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them, but do not preclude the presence or addition of one or more other features, integers, steps, operations, elements, components, and/or combinations thereof.

Figure 1:
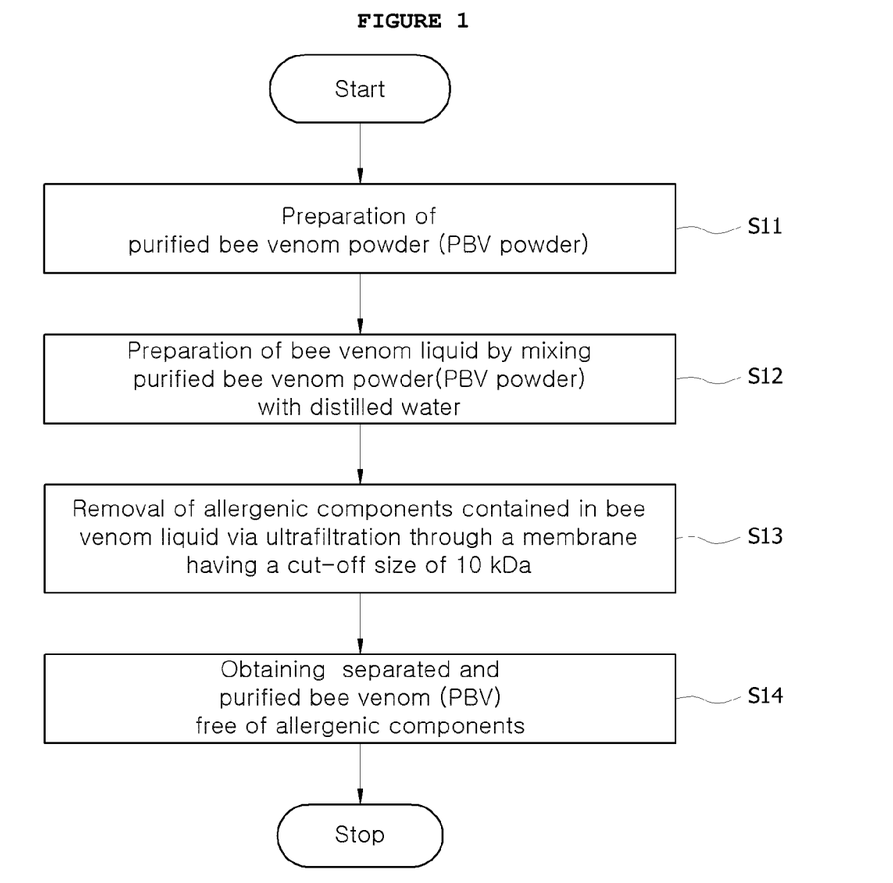
FIG. 1 is a flowchart illustrating a method of manufacturing a separated PBV according to an embodiment of the present invention.

FIG. 1 is a flowchart illustrating a method of manufacturing a separated PBV according to an embodiment of the present invention.

In manufacturing the separated PBV according to an embodiment of the present invention, the PBV powder may be prepared first (S11) as illustrated in FIG. 1. Here, the bee venom to be manufactured into the PBV may be collected from western honey bees, *Apis Mellifera*.

Here, the PBV powder may be prepared by various known methods in the related art. More specifically, the PBV powder may be prepared from bee venom collected from bees using a bee venom collector after the bee venom goes through a series of processes including natural drying, purification, sterilization and lyophilization, etc. The thus prepared PBV powder may have similar physiological activities to the raw bee venom collected from bees but the present invention is not limited thereto.

Then, the PBV powder is mixed with distilled water to prepare a bee venom liquid (S12). Preferably, the distilled water is in the range of from 1000 mL to 1500 mL per 1 g of the PBV powder.

When the distilled water to be mixed is less than 1000 mL the viscosity of the bee venom liquid increases, which lowers the bee venom liquid's permeability to an ultrafiltration membrane to be described later, thus decreasing the yield after ultrafiltration. In contrast, when greater than 1500 mL of distilled water is used the time required for ultrafiltration and drying becomes longer, thus reducing cost-effectiveness.

When the distilled water is used in the range of from 1000 mL to 1500 mL per 1 g of the PBV powder the yield of the separated PBV may be 60% or higher.

Subsequently, the bee venom liquid is filtrated by passing it through an ultrafiltration membrane having a cut-off size of 10 kDa, thereby removing allergenic components contained therein (S13).

The details of the approximate molecular weights of the major components contained in the PBV powder are shown in Table 2 below.

TABLE 2

| Category | Components | Molecular Weight |
|---|---|---|
| Protein Enzymes | phospholipase A2, B | >13 KDa |
| | hyaluronidase | 38 KDa |
| | phosphatase | 50-160 KDa |
| | α-glucosidase | 51 KDa |
| Peptides | Melittin | 2.8 KDa |
| | Apamine | 2.0 KDa |
| | MCD peptide | 2.6 KDa |
| | procamine, pamine | 0.4 KDa |
| | minimine | ≤6.0 KDa |
| | adolapine | 11.5 KDa |
| | protease inhibitor | 9.0 KDa |
| | fertiapine | ≤3.0 KDa |
| Active Amines & Amino Acids | histamine | 0.12 KDa |
| | dopamine | 0.15 KDa |
| | noradrenalin | 0.17 KDa |
| | aminobutyric acid | 0.18 KDa |
| | α-amino acids | |

As shown in Table 2, the molecular weight of phospholipase A2 and hyaluronidase, which are known as strong allergy-inducing components, is 13 kDa and 38 kDa, respectively. In the case of physiologically active materials such as ribosome, mitochondria, virus, etc., their molecular weights are roughly indicated in Dalton, and their size is estimated based on the molecular weight indicated as such.

Accordingly, the method of manufacturing the separated PBV according to an embodiment of the present invention is designed to prevent the penetration of any material with a size greater than 10 kDa by setting the cut-off size of the ultrafiltration membrane as such, thereby being capable of removing phospholipase A2 and hyaluronidase, which are allergenic components contained in the bee venom liquid. Furthermore, the manufacturing method of the present invention may include applying a pressure on the bee venom liquid during filtration to thereby speed up the filtration process and reduce the filtration time.

Subsequently, separated PBV without allergenic components is obtained (S14). Here, the separated PBV may contain 4 wt % or higher of apamin and 50 wt % or higher of melittin.

Figure 2:
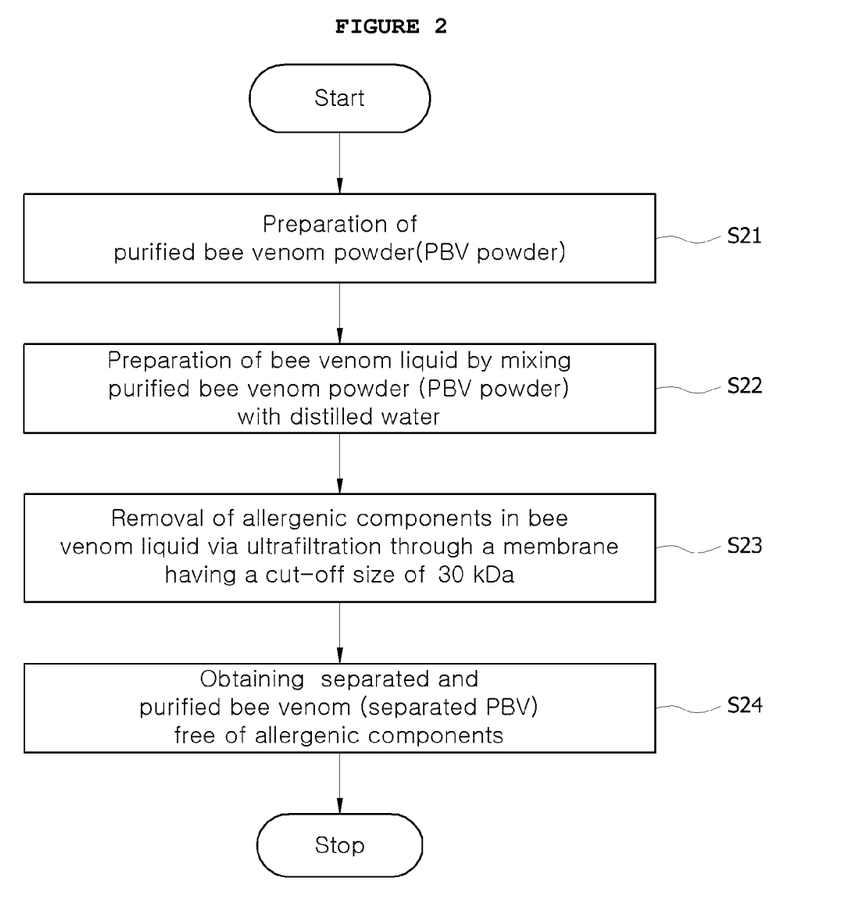
FIG. 2 is a flowchart illustrating a method of manufacturing a separated PBV according to another embodiment of the present invention.

FIG. 2 is a flowchart illustrating a method of manufacturing a separated PBV according to another embodiment of the present invention.

In manufacturing the separated PBV according to another embodiment of the present invention, the PBV powder is prepared first as shown in FIG. 2 (S21). Here, the PBV powder may be prepared in the same manner as in preparing the PBV according to an embodiment of the present invention.

Then, a bee venom liquid is prepared by mixing the PBV powder with distilled water (S22). Preferably, the distilled water may be used in the range of from 100 mL to 200 mL per 1 g of the PBV powder.

Then, the allergenic components contained in the bee venom liquid are removed by passing the bee venom liquid through an ultrafiltration membrane having a cut-off size of 30 kDa (S23).

In particular, when the distilled water to be mixed is less than 100 mL, the viscosity of the bee venom liquid increases, which lowers the bee venom liquid's permeability to an ultrafiltration membrane, thus decreasing the yield after ultrafiltration. In contrast, when the distilled water to be mixed is greater than 200 mL, as shown in FIG. 2, the concentration of phospholipase A2, as an allergenic component, is diluted while the permeability of phospholipase A2 to the ultrafiltration membrane increases, thus making it difficult to maximally reduce phospholipase A2, a strong allergy-inducing component of bee venom.

Accordingly, in manufacturing the separated PBV according to an another embodiment of the present invention, the distilled water to be mixed to prepare a bee venom liquid may be used in the range of from 100 mL to 200 mL per 1 g of the PBV, and the cut-off size of the ultrafiltration membrane may be set at 30 kDa, thereby removing hyaluronidase and maximally reducing phospholipase A2. Furthermore, the manufacturing method of the present invention may include applying pressure on the bee venom liquid during filtration to thereby speed up the filtration process and reduce the filtration time.

Subsequently, the separated PBV without allergenic components is obtained (S24). Here, the thus obtained separated PBV may contain 2.5 wt % or higher of apamin, 45 wt % or higher of melittin, and 1 wt % or less of phospholipase A2.

As described above, the method for manufacturing a separated PBV according to an embodiment of the present invention has the advantage that it can manufacture a separated PBV fundamentally safe from triggering allergic reactions by removing phospholipase A2 and hyaluronidase, which are strong inducers of allergic reactions.

Additionally, the method for manufacturing a separated PBV according to an another embodiment of the present invention has the advantage that it can manufacture a separated PBV fundamentally safe from triggering allergic reactions by removing hyaluronidase while maximally reducing phospholipase A2, both of which are strong inducers of allergic reactions.

Additionally, the method for manufacturing a separated PBV of the present invention has the advantage that the increase in the yield and a large-scale production of the separated PBV are enabled by removing the allergenic components contained in the PBV via ultrafiltration.

The cosmetic containing a separated PBV according to another embodiment of the present invention includes a separated PBV manufactured according to an embodiment or another embodiment of the present invention as an active ingredient.

As described above, the cosmetic containing a separated PBV according to another embodiment of the present invention includes the separated PBV manufactured according to a method of the present invention as an active ingredient, and thus has an advantage of having an anti-wrinkle effect and a whitening effect due to the bee venom contained therein while being fundamentally safe from triggering allergic reactions.

A better understanding of the present invention may be obtained through the following examples which are set forth to illustrate, but are not to be construed as the limit of the present invention.

Example 1

1) Preparation of PBV Powder

Bee venom was collected from western honey bees, *Apis mellifera*, via the electrical shock method. The collected bee venom was dissolved in distilled water, and filtered through a filter paper with fine pores of 3.0 μm on average formed therein to remove soils, dust, pollens, etc.

Then, the resultant was filtered through a membrane filter with fine pores having a size of from 0.45 to 0.2 μm to remove impurities and bacteria and then lyophilized to obtain a PBV powder.

2) Separation of Allergenic Components

The PBV powder prepared previously was mixed with distilled water, purified via filtration through a 0.2 μm membrane filter, in a ratio of 1:1000 (g/mL) to obtain a bee venom liquid.

Then, the bee venom liquid was filtered through an ultrafiltration membrane (Ultracel PL regenerated cellulose, 76 mm) with a cut-off size of 10 kDa using Millipore series 8400 stirred cells to remove allergenic components thereby obtaining a separated PBV. Here, the filtration was performed until the bee venom liquid contained in the cells was concentrated to a final volume of about from 5 mL to 10 mL under the pressure of 0.4 MPa.

The thus obtained separated PBV was dried into powder via lyophilization.

Example 2

1) Preparation of PBV Powder

PBV powder was prepared in the same manner as in Example 1.

2) Separation of Allergic Ingredients

The PBV powder prepared previously was mixed with distilled water, purified via filtration through a 0.2 μm membrane filter, in a ratio of 1:100 (g/mL) to obtain a bee venom liquid.

Then, the bee venom liquid was filtered through an ultrafiltration membrane (Ultracel PL regenerated cellulose, 76 mm) with a cut-off size of 30 kDa using Millipore series 8400 stirred cells to remove allergenic components thereby obtaining a separated PBV. Here, the filtration was performed until the bee venom liquid contained in the cells was concentrated to a final volume of about from 5 mL to 10 mL under the pressure of 0.4 MPa.

The thus obtained separated PBV was dried into powder via lyophilization.

Experimental Example 1

Electrophoresis Experiment

18% or 20% gel composition ((i) 18% gel composition consisting of 1.3 mL of distilled water, 6.0 mL of 30% acrylamide mix, 2.5 mL of 1.5 tris(hydroxymethyl)aminomethane-HCl (Tris-HCl) (pH8.8), 100 μL of 10% sodium dodecyl sulfate (SDS), 100 μL of 10% ammonium persulfate, and 4 μL of tetramethylethylenediamine (TEMED); and (ii) 20% gel composition consisting of 700 μL of distilled water, 6.6 mL of 30% acrylamide mix, 2.5 mL of 1.5 M Tris-HCl (pH8.8), 100 μL of 10% SDS, 100 μL of 10% ammonium persulfate, and 4 μL of TEMED) were prepared, and 10 mL each of the gel compositions was aliquoted onto a glass plate.

Upon equilibration, a separating gel was solidified, and then, about 5 mL of a stacking gel composition (consisting of 3.4 mL of distilled water, 830 μL of 30% acrylamide mix, 630 μL of 1.5 M Tris-HCl (pH 8.8), 50 μL of 10% SDS, 50 μL of 10% ammonium persulfate, and 5 μL of TEMED) was aliquoted. The gel was solidified after inserting a comb therein. Upon solidification of the stacking gel, the comb was removed and completed the preparation of an SDS-PAGE gel.

The fraction for SDS-PAGE gel electrophoresis and a sample buffer (Laemmli 2× Concentrate, sigma, 53401) were mixed in a 1:1 ratio, and then incubated in a water bath at 90° C. for 5 minutes. Then, 5 μL of a marker, and 30 μL each of a standard PBV, the separated PBVs prepared in Examples 1 and 2, apamin, phospholipase A2 and melittin were loaded into the wells of the gel, and the gel was inserted into an SDS-PAGE gel tank, and filled with a running buffer (25 mM Tris, 192 mM glycine, 0.1% SDS, pH 8.3).

The SDS-PAGE gel electrophoresis was performed in a stacking gel at 60 V for 30 minutes using an SDS-PAGE power supply, and in a separating gel at 120 V for from 60 to 90 minutes.

The components contained in the sample were separated in the gel triggered by the current being provided by the power supply according to their molecular weight. The gel was stained with coomassie brilliant blue R-250 dye and then destained with a destaining solution, and the resulting gel is shown in FIG. 3.

Figure 3:
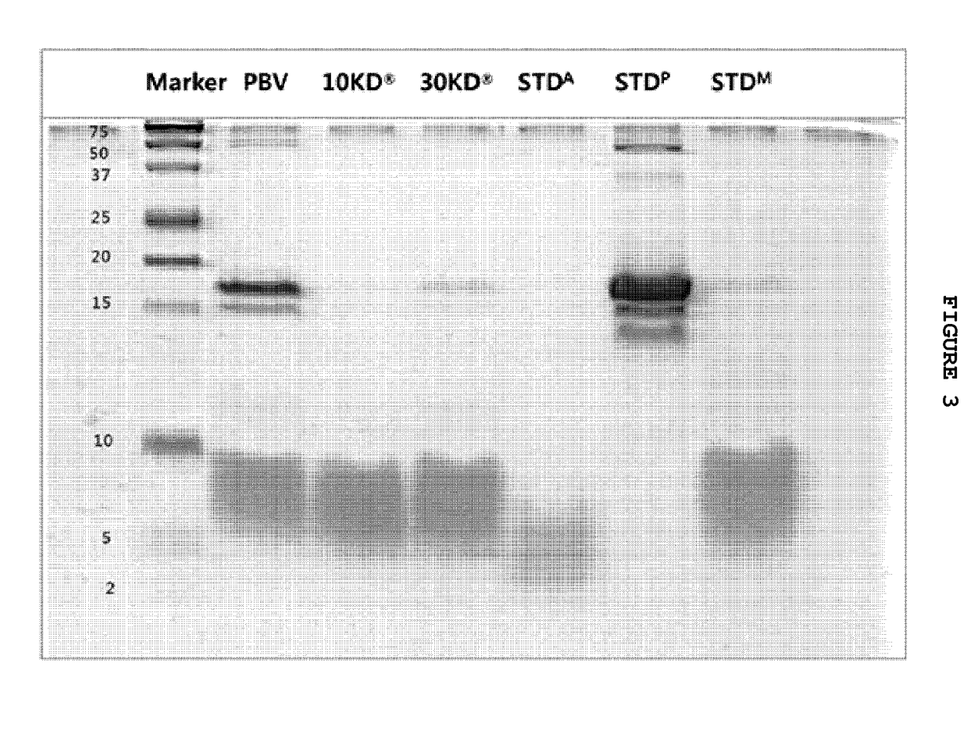
FIG. 3 shows a result of gel electrophoresis according to Experimental Example 1 of the present invention.

FIG. 3 shows a result of gel electrophoresis according to Experimental Example 1 of the present invention.

The bands representing the standard PBV, the separated PBVs prepared in Examples 1 and 2 (10 kDa, 30 kDa), apamin (99.9% of apamin, STDA), phospholipase A2

(PLA2 90.7%, STDP) and melittin (96% of melittin, STDM) in the gel electrophoresis, as shown in FIG. 3, were compared.

The result showed that the phospholipase A2 band, which should appear in the region of the gel representing a molecular weight of from 15 to 20 kDa, was missing in the lane for the separated PBV prepared in Example 1 thus confirming that phospholipase A2 was removed from the separated PBV of Example 1, whereas the phospholipase A2 band was barely seen in the lane for the separated PBV of Example 2 thus confirming phospholipase A2 was significantly reduced in the separated PBV of Example 2. Additionally, the hyaluronidase band, which should appear in the region representing 50 kDa, was missing in both lanes for the separated PBVs of Examples 1 and 2, thus confirming that hyaluronidase was removed from the separated PBVs of Examples 1 and 2.

Experimental Example 2

HPLC Quantitative Analysis

The separated PBVs of Examples 1 and 2 were respectively prepared into a concentration of 1.0 mg/mL, and analyzed via high-performance liquid chromatography (HPLC) apparatus using a peptide analysis column (150×4.6 mm 4.0 μm, 90, Phenomenex®) along with water for HPLC (0.2% TFA in water), and acetonitrile (0.22% TFA in ACN) as a solvent.

Figure 4:
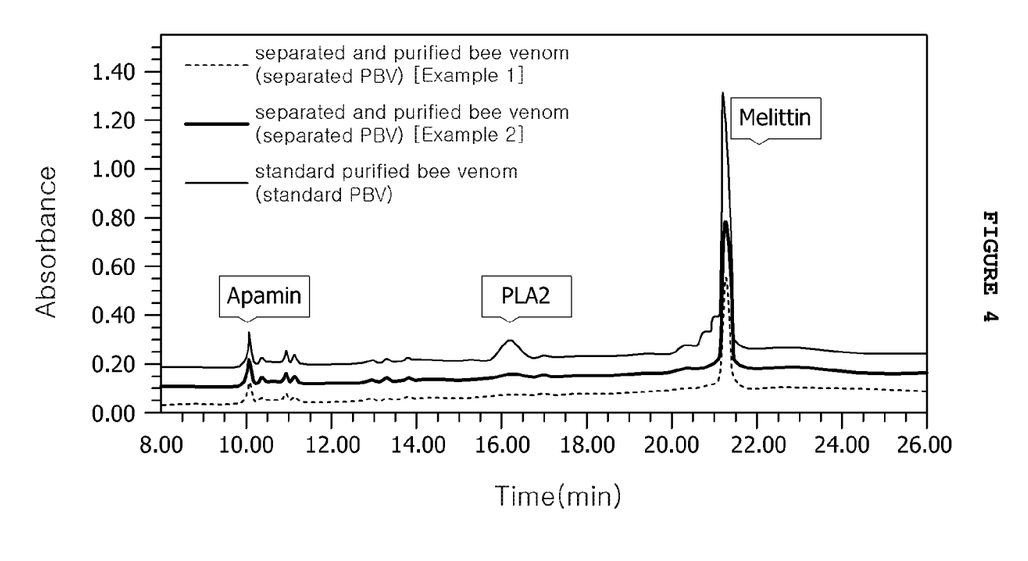
FIG. 4 is a graph showing a result of high-performance liquid chromatography (HPLC) analysis of the separated PBVs according to Experimental Example 2 of the present invention.

FIG. 4 is a graph showing a result of HPLC analysis of the separated PBVs according to Experimental Example 2 of the present invention.

As a result of HPLC quantitative analysis, the components contained in each of the separated PBVs of Examples 1 and 2 were confirmed in comparison with those of the standard PBV, as shown in FIG. 4.

More specifically, an HPLC quantitative analysis result of the standard PBV revealed that apamin and melittin had peaks at 10.4 min and 21.3 min, respectively, and phospholipase A2(PLA2) had a peak at 16.3 min.

The area of a given peak can be used to calculate contents, in particular, by the Equation 1 below.

$$\text{Content (\%)} = \frac{\text{collected amount of a standard material (mg)} \times \frac{\text{purity of a standard material (\%)}}{100} \times \frac{\text{peak area of a sample liquid}}{\text{peak area of a standard material}}}{\text{collected amount of a sample}} \times 100 \quad <\text{Equation 1}>$$

When the sample liquid in the Equation 1 was substituted with the PBVs of Example 1 and Example 2, respectively, the results are as shown below.

TABLE 3

| Sample Fraction | Components | | |
|---|---|---|---|
| | Apamin (%) | PLA2 (%) | Melittin (%) |
| Standard purified bee venom | 2.4 | 12.52 | 58.25 |
| Separated PBV (Ex. 1) | 4.05 | — | 54.5 |
| Separated PBV (Ex. 2) | 2.81 | ≤1.0 | 46.77 |

Accordingly, it was confirmed that PLA2 is absent in the separated PBV of Example 1, and PLA2 is contained 1 wt % or less in the separated PBV of Example 2, at a maximally reduced level.

Experimental Example 3

Anti-Wrinkle Effect

Elastase Inhibitory Effect

In this experiment, 20 μL each of a standard PBV, and separated PBVs of Examples 1 and 2, was added to 200 μL of 0.1 mM of N-succinly-(Ala)3-p-nitroanilide, used as a substrate. Each of the mixture was then added with 10 μL of 0.1 mg/mL of elastase (porcine pancreas solution) and allowed to react at 25° C. for 10 minutes. The resultants were measured of their absorbance at 410 nm via an enzyme-linked immunosorbent assay (ELISA) reader, and their inhibition rate (%) on elastase was calculated thereby confirming their anti-wrinkle effects.

Figure 5:
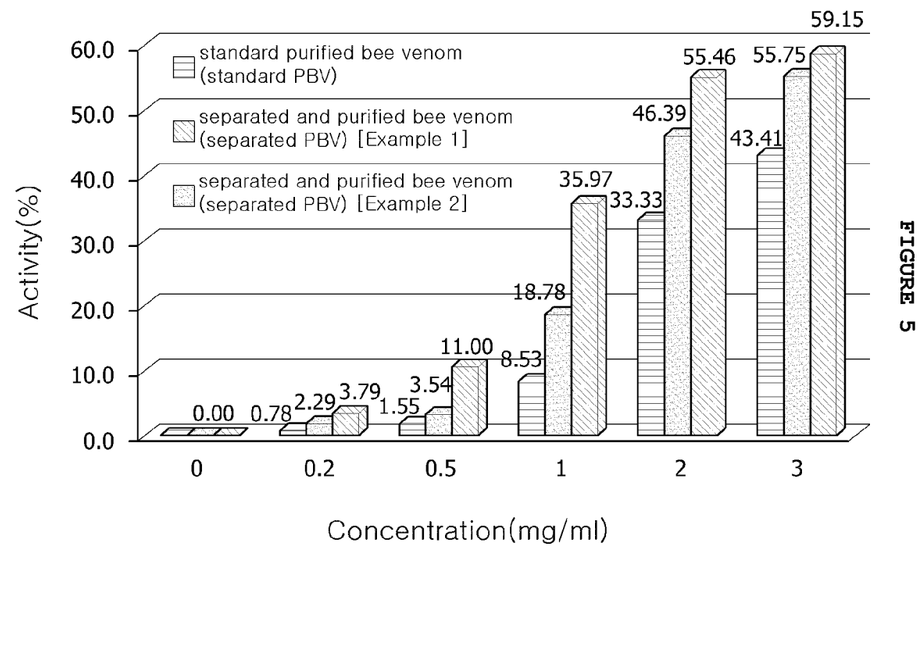
FIG. 5 is a graph showing a test result of the separated PBVs on their anti-wrinkle effects according to Experimental Example 3 of the present invention.

FIG. 5 is a graph showing a test result of the separated PBVs on their anti-wrinkle effects according to Experimental Example 3 of the present invention.

Upon reviewing the anti-wrinkle effects of the standard PBV and the separated PBVs of Examples 1 and 2, it was confirmed, as shown in FIG. 5, that both of the separated PBVs of Examples 1 and 2 had superior anti-wrinkle effects at various concentrations (0.2 mg/mL, 0.5 mg/mL, 1 mg/mL, 2 mg/mL and 3 mg/mL) to that of the standard PBV.

Experimental Example 4

Whitening Effect

Tyrosinase Inhibitory Effect

In this experiment, a substrate was prepared by dissolving 21.2 mg of tyrosine in 46.8 mL of 0.1 M phosphate buffered saline (PBS) (pH6.8). Additionally, experimental liquids were prepared by mixing each of the standard PBA and the separated PBVs of Examples 1 and 2 in distilled water, respectively.

Each of the experimental liquids in the amount of 300 μL was mixed with 225 μL of the substrate. Each of the mixtures was added with 107 μL of tyrosinase (diluted to 210 U/mL in PBS before use) and then with PBS to a final volume of 900 μL, and incubated at 37° C. for 15 minutes, respectively. The resultants were measured of their absorbance at 480 nm via a microplate reader and ELISA, and their whitening effects were examined.

Figure 6:
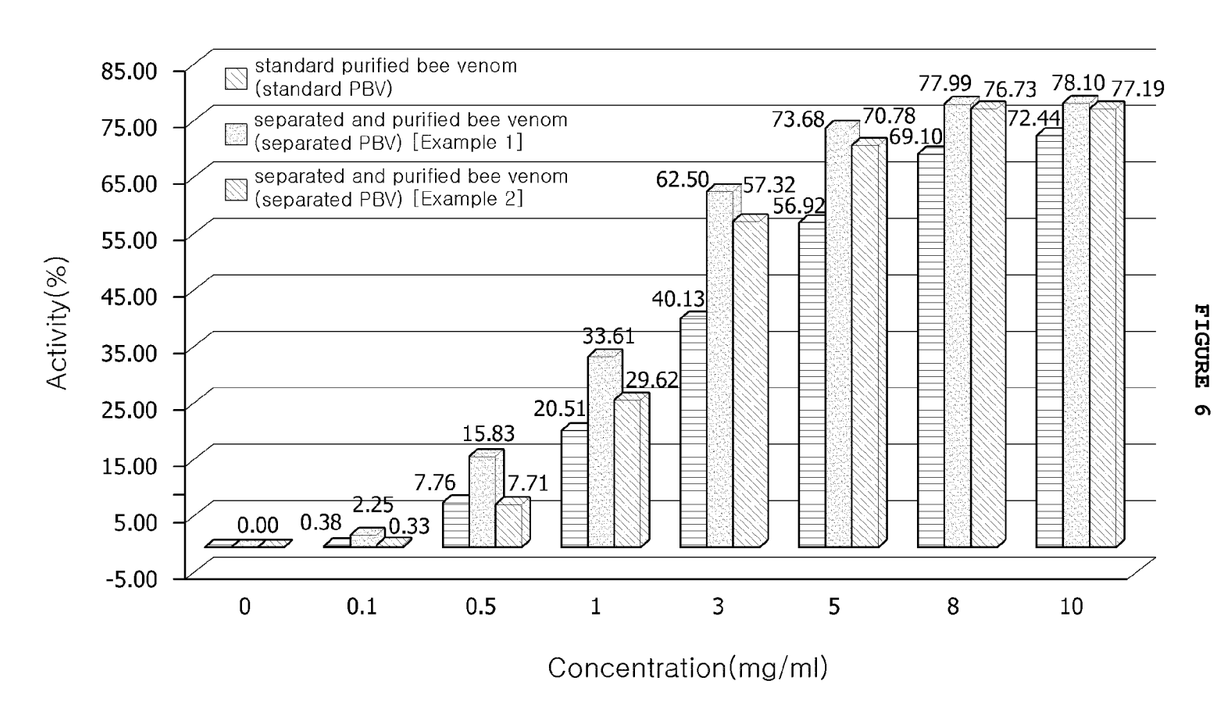
FIG. 6 is a graph showing a test result of the separated PBVs on their whitening effects according to Experimental Example 4 of the present invention.

FIG. 6 is a graph showing a test result of the separated PBVs and their whitening effects according to Experimental Example 4 of the present invention.

Upon reviewing the whitening effects of the standard PBV and the separated PBVs of Examples 1 and 2, it was confirmed, as shown in FIG. 6, that both of the separated PBVs of Examples 1 and 2 had superior whitening effects at various concentrations (0.1 mg/mL, 0.5 mg/mL, 1 mg/mL, 3 mg/mL, 5 mg/mL, 8 mg/mL and 10 mg/mL) to that of the standard PBV.

Experimental Example 5

Disc Diffusion Method

The standard PBV, and separated PBVs of Examples 1 and 2 at various concentrations were respectively absorbed onto a disc, in which an experimental bacteria strain was cultured, and then each disc was inoculated using a dispenser onto a solid culture medium in which the bacteria strain was cultured. After culturing for from 16 to 18 hours, the antibacterial effect was examined by comparing the size of the inhibition zone between the separated PBVs of Examples 1 and 2 with that of a control group, in which the standard PBV was used.

To verify the antibacterial effect of the separated PBVs of Examples 1 and 2 according to Experimental Example 5, three different indicator bacteria strains (*Staphylococcus aureus* and *Streptococcus mutans* as gram positive bacteria, and *Salmonella typhimurium* as gram negative bacteria) were kindly provided by Korean Culture Center of Microorganisms (KCCM).

More specifically, the bacterial strains were sub-cultured in liquid media for 24 hours, and then the indicator strains were activated. When the number of indicator strains was confirmed that the optical density of the indicator strains at 660 nm was in the range of from 0.5 to 0.7, a certain amount of the culture liquid of the indicator strains was aliquoted into a solid medium and plated thereon using a triangular sterilized glass spreader. Then, a paper disc was put on top of the solid medium with the indicator strains plated thereon, and 40 µL each of the standard PSV, and the separated PBVs of Examples 1 and 2 at various concentrations were loaded thereto.

The petri dishes containing the PBVs were cultured in an incubator for from 18 to 24 hours, and the resulting comparative size of clear zones is shown in Table 4 below.

TABLE 4

| Bacteria Strain | Standard PBV | Separated PBV (Ex. 1) | Separated PBV (Ex. 2) |
|---|---|---|---|
| S. aureus | 10 mm | 10 mm | 10 mm |
| S. mutans | 13 mm | 12 mm | 12 mm |
| S. typhimurium | 10 mm | 10 mm | 10 mm |

(In the above, *S. aureus* stands for *Staphylococcus aureus*, *S. mutans* stands for *Streptococcus mutans*, and *S. typhimurium* stands for *Salmonella typhimurium*.)

Referring to Table 4, it was confirmed that the active ingredients of the separated PBVs of Examples 1 and 2 had the same level of antibacterial effect as those of the standard PBV, thus confirming that the separated PBVs of the present invention can surely exhibit a significant antibacterial effect while fundamentally blocking the occurrence of allergies.

Experimental Example 6

Method of Testing Minimum Inhibitory Concentration (MIC)

*Salmonella typhimurium* and *Staphylococcus aureus* were cultured in luria-bertani (LB) broth, and *Streptococcus epidermidis* was cultured in brain heart infusion (BHI) broth, both for 24 hours before use. The standard PBV and the separated PBVs of Examples 1 and 2 were diluted to half of its concentration in distilled water to prepare experimental liquids at various concentrations.

Prior to inoculation of the strains, their initial concentration was estimated by measuring their absorbance at 650 nm, and each tube was added with a pure liquid culture medium and the standard PBV and the separated PBVs of Examples 1 and 2 according to the concentration, and then inoculated with a certain amount of the strains.

After culturing at 37° C. for 24 hours, the absorbance of the cultures were measured at 650 nm. The sample concentration which showed the same result as in the pure liquid culture medium was determined as its MIC. The inhibition rate against the bacterial strains was calculated by the Equation 2 below and the results are shown in Table 5 below.

Inhibition rate(%)=[1−(absorbance of a sample-treated group/absorbance of control group)]×100     <Equation 2>

TABLE 5

| | Inhibition rate (%)/MIC (µg/mL) | | |
|---|---|---|---|
| | Standard PBV | Separated PBV (Ex. 1) | Separated PBV (Ex. 2) |
| S. typhimurium | 99.9%; >64 | 99.9%; >2 | 99.9%; >2 |
| S. aureus | 99.5%; >16 | 74.7%; >4 | 99.9%; >8 |
| S. epidermidis | 97.1%; >64 | 99.9%; >8 | 99.9%; >4 |

(In the above, *S. typhimurium* stands for *Salmonella typhimurium*, *S. aureus* stands for *Staphylococcus aureus* (S.A), and *S. epidermidis* stands for *Staphylococcus epidermidis* (S.E).)

Referring to Table 5, it was confirmed that the separated PBVs of Examples 1 and 2 had a superior MIC effect to that of the standard PBV while having the same level of bacteria inhibition rate as that of the standard PBV.

Accordingly, it was confirmed that the separated PBVs of Examples 1 and 2 can exhibit a significant antibacterial effect while being capable of preventing allergies at the same time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, the separated PBV of the present invention can be used in various industrial fields such as pharmaceuticals, foods, and cosmetics, which may include PBV as a raw material.

The invention claimed is:

1. A method for manufacturing a separated and purified bee venom (separated PBV), comprising:
    a first step of preparing a purified bee venom powder;
    a second step of preparing a bee venom liquid by mixing the purified bee venom powder with distilled water;
    a third step of removing allergenic components contained in the bee venom liquid via ultrafiltration through a membrane having a cut-off size of 10 kDa; and
    a fourth step of obtaining a separated PBV with allergenic components removed;
    wherein the distilled water to be mixed with the purified bee venom powder in the second step is used in the range of from 1000 mL to 1500 mL per 1 g of the purified bee venom powder;
    the allergenic components removed through the ultrafiltration membrane in the third step are phospholipase A2 and hyaluronidase; and the separated PBV obtained in the fourth step comprises 4 wt % or higher of apamin, and 50 wt % or higher of melittin.

2. A method for manufacturing a separated PBV, comprising:

a first step of preparing a purified bee venom powder;
a second step of preparing a bee venom liquid by mixing the purified bee venom powder with distilled water;
a third step of removing allergic ingredients contained in the bee venom liquid via ultrafiltration through a membrane having a cut-off size of 30 kDa; and
a fourth step of obtaining a separated PBV with an allergenic component removed;
wherein the distilled water to be mixed with the purified bee venom powder in the second step is used in the range of from 100 mL to 200 mL per 1 g of the purified bee venom powder; the allergenic component removed through the ultrafiltration membrane in the third step is hyaluronidase; and the separated PBV obtained in the fourth step comprises 2.5 wt % or higher of apamin, 45 wt % or higher of melittin[1], and 1 wt % or less of phospholipase A2.

* * * * *